(12) United States Patent
Kobayashi et al.

(10) Patent No.: US 11,615,125 B2
(45) Date of Patent: Mar. 28, 2023

(54) RELEVANCE SEARCHING METHOD, RELEVANCE SEARCHING APPARATUS, AND STORAGE MEDIUM

(71) Applicant: FUJITSU LIMITED, Kawasaki (JP)

(72) Inventors: Kenichi Kobayashi, Kawasaki (JP); Shinichiro Tago, Shinagawa (JP); Hirotaka Shibata, Yokohama (JP); Haruyasu Ueda, Ichikawa (JP)

(73) Assignee: FUJITSU LIMITED, Kawasaki (JP)

( * ) Notice: Subject to any disclaimer, the term of this patent is extended or adjusted under 35 U.S.C. 154(b) by 433 days.

(21) Appl. No.: 16/850,631

(22) Filed: Apr. 16, 2020

(65) Prior Publication Data

US 2020/0342015 A1    Oct. 29, 2020

(30) Foreign Application Priority Data

Apr. 25, 2019 (JP) .............................. JP2019-084188

(51) Int. Cl.
*G06F 16/33* (2019.01)
*G16B 40/00* (2019.01)
(Continued)

(52) U.S. Cl.
CPC ........ *G06F 16/3328* (2019.01); *G06F 16/338* (2019.01); *G06F 16/3331* (2019.01);
(Continued)

(58) Field of Classification Search
CPC ............. G06F 16/3328; G06F 16/3331; G06F 16/338; G06K 9/6296; G06N 7/005;
(Continued)

(56) References Cited

U.S. PATENT DOCUMENTS

2004/0059521 A1* 3/2004 Han ....................... G16B 45/00
702/19
2004/0059522 A1* 3/2004 Han ....................... G16B 45/00
702/19
(Continued)

FOREIGN PATENT DOCUMENTS

JP       2007-128163 A    5/2007
JP       2010-66814       3/2010
(Continued)

OTHER PUBLICATIONS

Zhang et al., "Long Noncoding RNA and Protein Interactions: From Experimental Results to Computational Models Based on Network Models", International Journal of Molecular Sciences, 2019, 20, 1284, pp. 1-30 (Year: 2019).*

(Continued)

*Primary Examiner* — Nay A Maung
*Assistant Examiner* — Jose M Torres
(74) *Attorney, Agent, or Firm* — Fujitsu Patent Center

(57) ABSTRACT

A relevance searching method performed by a computer, the relevance searching method includes generating a combined database by combining a plurality of databases each including a plurality of elements and relevance information indicating direct relevance between two elements in the plurality of elements; and searching for relevance between two elements that do not have direct relevance by using the combined database.

15 Claims, 26 Drawing Sheets

(51) Int. Cl.
*G16B 35/20* (2019.01)
*G06F 16/332* (2019.01)
*G06F 16/338* (2019.01)
*G06N 20/00* (2019.01)
*G16B 50/30* (2019.01)
*G06K 9/62* (2022.01)

(52) U.S. Cl.
CPC ........... *G06K 9/6296* (2013.01); *G06N 20/00* (2019.01); *G16B 35/20* (2019.02); *G16B 40/00* (2019.02); *G16B 50/30* (2019.02)

(58) Field of Classification Search
CPC ........ G06N 20/00; G16B 35/20; G16B 40/00; G16B 50/30
See application file for complete search history.

(56) References Cited

U.S. PATENT DOCUMENTS

| | | | |
|---|---|---|---|
| 2007/0286218 A1* | 12/2007 | Zhang | H04L 45/123 370/401 |
| 2008/0059455 A1* | 3/2008 | Canoy | G06Q 10/10 707/999.005 |
| 2011/0159513 A1 | 6/2011 | Schoeberl et al. | |
| 2011/0173189 A1* | 7/2011 | Singh | G06F 16/9024 707/722 |
| 2012/0158391 A1 | 6/2012 | Vaske et al. | |
| 2013/0268357 A1* | 10/2013 | Heath | G06Q 10/10 726/26 |
| 2013/0315885 A1 | 11/2013 | Narain et al. | |
| 2013/0331433 A1* | 12/2013 | Thibonnier | C12Q 1/6883 435/375 |
| 2014/0280224 A1* | 9/2014 | Feinberg | G06F 16/9024 707/748 |
| 2017/0329914 A1* | 11/2017 | Assefa | G16B 20/20 |
| 2019/0259470 A1* | 8/2019 | Olafson | G16B 40/00 |

FOREIGN PATENT DOCUMENTS

| | | |
|---|---|---|
| JP | 2010-165230 A | 7/2010 |
| JP | 2012-500008 A | 1/2012 |
| JP | 2017-182813 A | 10/2017 |
| JP | 2018-049017 A | 3/2018 |

OTHER PUBLICATIONS

JPOA—Japanese Office Action dated Nov. 8, 2022 for corresponding Japanese Patent Application No. 2019-084188 with Machine Translation.

* cited by examiner

FIG. 8

| RANK | THERAPEUTIC AGENT | TARGET PROTEIN | PATH ACTION PROBABILITY |
|---|---|---|---|
| 1 | MEDICINE 2 | P15 | 0.1152 |
| 2 | MEDICINE 1 | P5 | 0.1000 |
| 3 | MEDICINE 3 | P25 | 0.09216 |

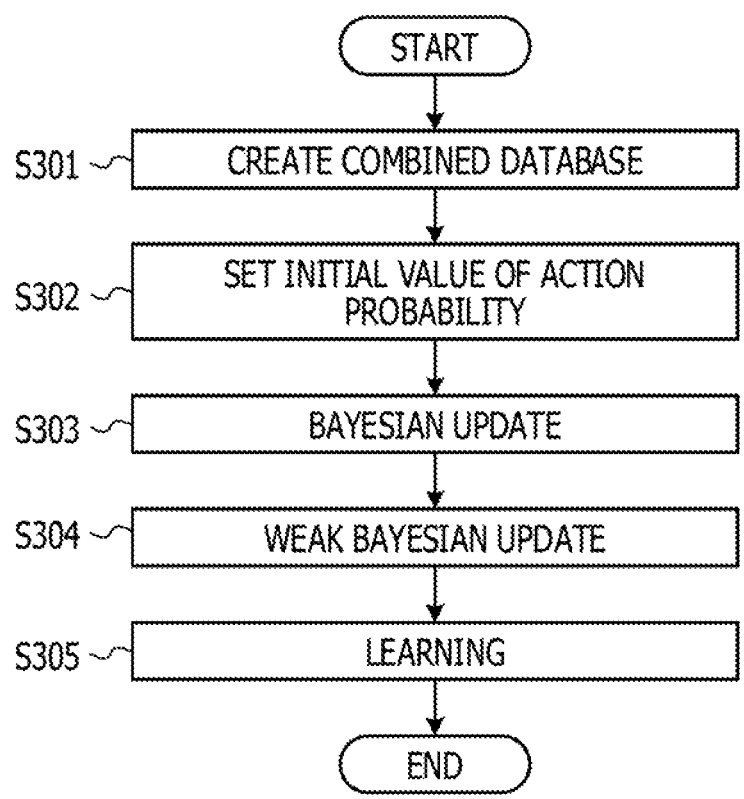

RELEVANCE SEARCHING METHOD, RELEVANCE SEARCHING APPARATUS, AND STORAGE MEDIUM

CROSS-REFERENCE TO RELATED APPLICATION

This application is based upon and claims the benefit of priority of the prior Japanese Patent Application No. 2019-84188, filed on Apr. 25, 2019, the entire contents of which are incorporated herein by reference.

FIELD

The embodiment discussed herein is related to a relevance searching method, a relevance searching apparatus, and a storage medium.

BACKGROUND

In a known database, usually, relevance between pieces of information in a database may be searched for by a network built in the database (see, for example, Patent Document 1).

However, in many cases in the world, there is relevance between pieces of information that may not be searched for from only a single database. For example, related arts are disclosed in Japanese Laid-open Patent Publication No. 2007-128163, and so on.

SUMMARY

According to an aspect of the embodiments, a relevance searching method performed by a computer, the relevance searching method includes generating a combined database by combining a plurality of databases each including a plurality of elements and relevance information indicating direct relevance between two elements in the plurality of elements; and searching for relevance between two elements that do not have direct relevance by using the combined database.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 3C is graph structure of a combined database in which FIG. 3A and FIG. 3B are combined;

FIG. 8 is an example of presentation of results;

FIG. 10 is a flowchart for explaining an example of setting an action probability;

FIG. 16C is an example of graph structure of a combined database in which FIG. 16A and FIG. 16B are combined;

DESCRIPTION OF EMBODIMENTS

It is desirable to provide a relevance searching method, a relevance searching apparatus, and a relevance searching program capable of searching for relevance between elements that may not be searched for from only a single database.

Relevance Searching Method, Relevance Searching Apparatus, and Relevance Searching Program The relevance searching method in the present embodiment combines a plurality of databases each including a plurality of elements, and relevance information indicating direct relevance between two elements in the plurality of elements, to create a combined database.

The relevance searching method further uses the combined database to search for relevance between two elements that do not have direct relevance.

The relevance searching method, for example, presents relevance between two elements that are determined to have relevance but do not have direct relevance.

The relevance searching apparatus in the present embodiment at least includes a creation unit and a searching unit, and further includes a presentation unit, as appropriate.

The creation unit combines a plurality of databases each including a plurality of elements, and relevance information indicating direct relevance between two elements in the plurality of elements, to create a combined database.

The searching unit uses the combined database to search for relevance between two elements that do not have direct relevance.

The presentation unit presents relevance between two elements that are determined to have relevance but do not have direct relevance.

The relevance searching program in the present embodiment causes a computer to combine a plurality of databases each including, a plurality of elements, and relevance information indicating direct relevance between two elements in the plurality of elements, to create a combined database.

The relevance searching program further causes the computer to use the combined database to search for relevance between two elements that do not have direct relevance.

The relevance searching program, for example, further causes the computer to present relevance between two elements that do not have direct relevance.

Structure of the combined database is, for example, graph structure in which an element is a node, and relevance information is an edge.

The relevance information is, for example, information indicating strength of relevance between two elements.

In each database, it is not demanded that relevance information of all combinations of arbitrary two elements among all elements exist.

In the relevance searching method, the relevance searching apparatus, and the relevance searching program in the present disclosure, for example, relevance between elements that may not be searched for only from a single database is searched for as follows.

Figure 1:
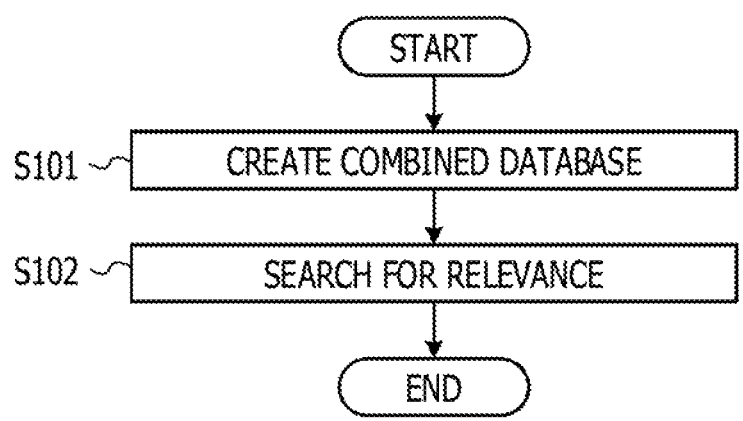
FIG. 1 is a flowchart of an example of a method of searching for relevance.
Figure 2:
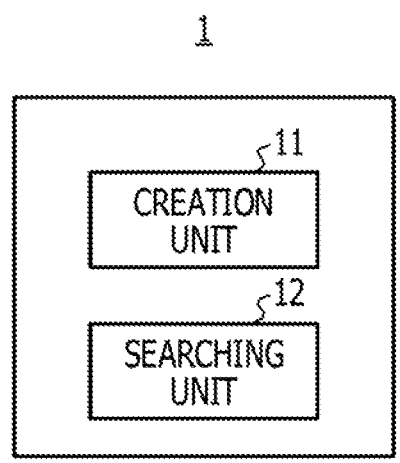
FIG. 2 is a configuration diagram of an example of a relevance searching apparatus.

FIG. 1 illustrates a flowchart of an example of a method of searching for relevance. FIG. 2 illustrates a configuration diagram of a relevance searching apparatus 1.

Step S101

First, a combined database is created (S101). The creation of the combined database is performed, for example, in a creation unit 11 of the relevance searching apparatus 1.

Figure 3A:
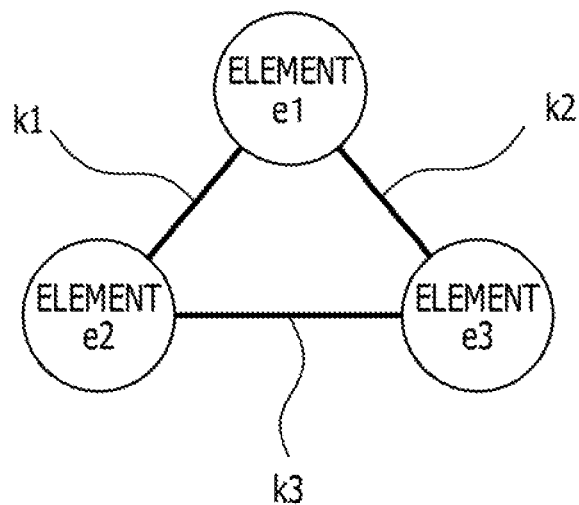
FIG. 3A is an example of graph structure of a first database.
Figure 3B:
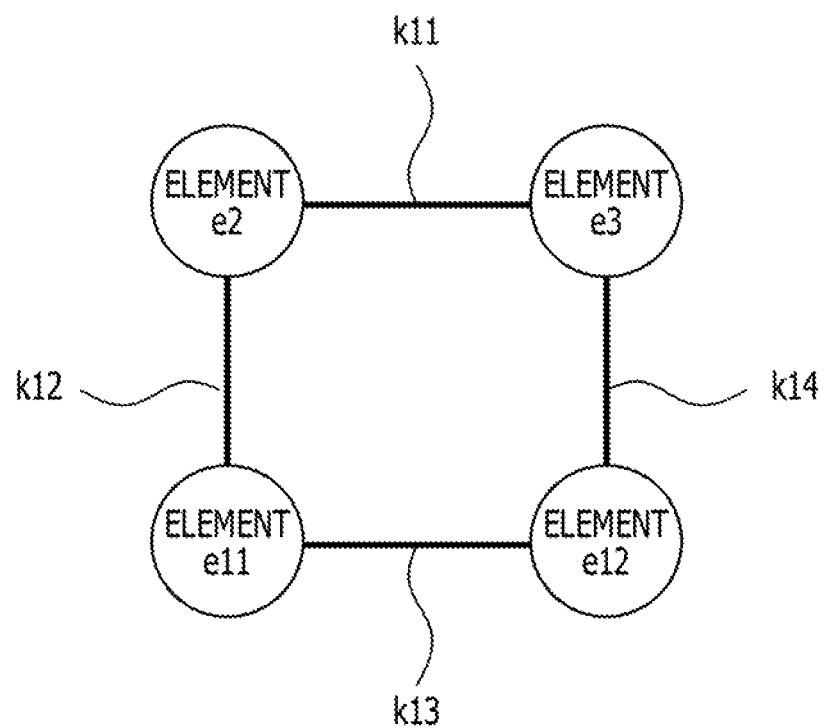
FIG. 3B is an example of graph structure of a second database.
Figure 3C:
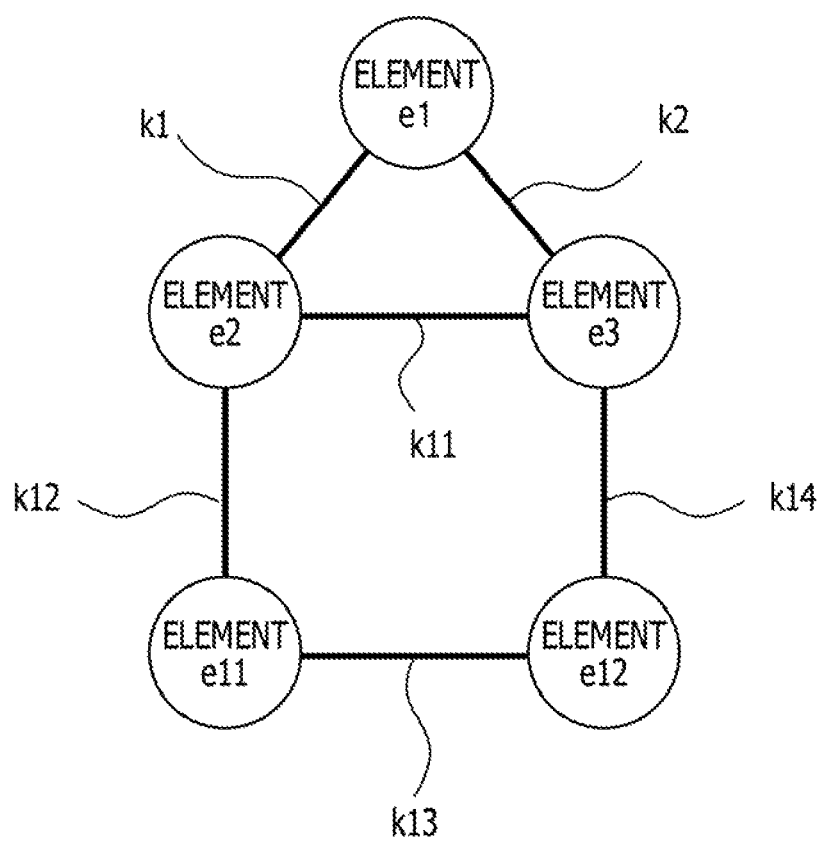

In Step S101, for example, a first database having graph structure illustrated in FIG. 3A, and a second database having graph structure illustrated in FIG. 3B are combined to create a combined database having graph structure illustrated in FIG. 3C.

The first database has an element e1 to an element e3, and relevance information k1 to relevance information k3 between respective two elements. The graph structure illustrated in FIG. 3A is graph structure in which each of the element e1 to element e3 is a node, and each of the relevance information k1 to relevance information k3 is an edge.

The second database has an element e2, an element e3, an element e11, and an element e12, and relevance information k11 to relevance information k14 between respective two elements. The graph structure illustrated in FIG. 3B is graph structure in which each of the element e2, the element e3, the element e11, and the element e12 is a node, and each of the relevance information k11 to relevance information k14 is an edge.

In the creation of the combined database, for example, duplicate elements are integrated into one element.

The combined database in which the first database and the second database are combined includes, as illustrated in FIG. 3C, the element e1, the element e2, the element e3, the element e11, and the elements e12, and the relevance information k1, the relevance information k2, and the relevance information k11 to the relevance information k14 between the respective two elements. The graph structure illustrated in FIG. 3C is graph structure in which each of the element e1, the element e2, the element e3, the element e11, and the element e12 is a node, and each of the relevance information k1, the relevance information k2, and the relevance information k11 to the relevance information k14 is an edge.

When the combined database is created, and there are pieces of relevance information that are different from each other between two elements (for example, when there are the relevance information k3 and the relevance information k11 different from each other between the element e2 and the element e3), the combined database may be created using any of the pieces of relevance information. Relevance information is preferably updated, by using learning data, after the combined database is created.

The number of databases to be combined is not limited to two, and may be three or more.

Step S102

Next, the combined database is used to search for relevance between two elements that do not have direct relevance (S102). The search for relevance between two elements is performed, for example, in a searching unit 12 of the relevance searching apparatus 1.

For example, the combined database having the graph structure illustrated in FIG. 3C is used to search for relevance between the element e1 and the element e11 that do not have direct relevance. This relevance may not be found in the first database alone having the graph structure illustrated in FIG. 3A, or in the second database alone having the graph structure illustrated in FIG. 3B. Strength of the relevance between the elements e1 and e11 is calculated, for example, by totaling a plurality of pieces of relevance information present in one path between the element e1 and the element e11.

The database used in the relevance searching method, the relevance searching apparatus, and the relevance searching program in the present embodiment is not particularly limited, and may be appropriately selected according to a purpose, and examples thereof include the following databases.

A database in which interaction information between proteins is recorded

A database in which a friendship between person names is recorded

The relevance searching method, the relevance searching apparatus, and the relevance searching program may be used, for example, for searching/recommending a therapeutic agent, searching for a friendship, and the like, that may not be searched for from an existing single database.

Search and Recommendation of a Therapeutic Agent

The relevance searching method, relevance searching apparatus, and relevance searching program may be used to search for and recommend a therapeutic agent that may not be searched for from an existing single database.

There are many diseases such as cancer that occur due to genetic mutations. The genetic mutations may be examined by performing genetic analysis of a patient. For treatment of a disease caused by genetic mutation, a molecular targeted therapeutic agent acting directly on a protein has been effective.

However, a protein generated from a mutated gene causing a disease (hereinafter sometimes referred to as a "mutant protein") is not necessarily equal to a protein on which a molecular targeted therapeutic agent directly acts (hereinafter sometimes referred to as a "target protein"). Thus, identification of a molecular targeted therapeutic agent effective for genetic mutation is demanded for an effective treatment.

In the past, search for a therapeutic agent is performed by a procedure in which, a database in which a path to a protein called a pathway for which an action is experimentally confirmed is accumulated is used, a pathway is searched for that includes a path from a mutant protein to a target protein from the pathways, and investigation is performed to determine whether or not the pathway is effective. Since a pathway indicates presence or absence and a type, of an action, and the pathway does not directly indicate effectiveness of a medicine, thus intervention of a medical knowledge holder is demanded.

As support using a computer for the above procedure, a method of supporting enumeration by searching from a pathway database, a method of performing simulation by using a method such as a Petri net using information of a pathway, to support determination, and the like, are performed.

However, these methods are technologies premised on a known pathway, and thus may not find an unknown medicinal effect.

On the other hand, there has been proposed a method of statistically estimating a pathway by using a Bayesian network, or the like, as well.

However, what is obtained by this method is only graph structure of pathways, and information that is not statistically obtained such as a branching condition or a merging condition associated with a known pathway is lacking.

There has been proposed a method of estimating presence or absence of medicinal effects by examining attributes of proteins for a one to one relationship between the proteins.

However, in this method, it is impossible to perform estimation for a path which is composed of a plurality of protein relationships (for example, a path length of two or more).

By using an example of the relevance searching method, the relevance searching apparatus, and the relevance searching program in the present disclosure, a therapeutic agent having a medicinal effect for a disease may be presented not only for a known therapeutic agent, but also for an unknown therapeutic agent. The method will be described below.

In the following, when the relevance searching method is used for presenting a therapeutic agent, the method is referred to as a therapeutic agent presentation method. When the relevance searching apparatus is used for presenting a therapeutic agent, the apparatus is referred to as a therapeutic agent presentation apparatus. When the relevance searching program is used for presenting a therapeutic agent, the program is referred to as a therapeutic agent presentation program.

In the therapeutic agent presentation method in the present disclosure, first, a plurality of databases each including, information of a plurality of proteins, and interaction information indicating an interaction between two proteins in the plurality of proteins, is combined to create a combined database.

The plurality of databases satisfies at least one of the following (1) and (2).

(1) The plurality of databases includes a database having information of a mutant protein generated from a mutant gene, and a database having information of a target protein on which a therapeutic agent directly acts.

(2) The plurality of databases includes a database having information of a mutant protein generated from a mutant gene, and information. of a target protein on which a therapeutic agent directly acts.

Thus, the combined database has the information of the mutant protein generated from the mutant gene, and the information of the target protein on which the therapeutic agent directly acts.

In the therapeutic agent presentation method, the combined database is further used to search for relevance between a mutant protein and a target protein.

In the therapeutic agent presenting method, a therapeutic agent acting on a target protein that is determined to have relevance to a mutant protein is presented as a therapeutic agent for a disease caused by the mutant protein.

Examples of the protein information include, for example, a protein name, an amino acid sequence, and the like.

In the therapeutic agent presentation apparatus in the present disclosure includes a creation unit for combining a plurality of databases including information of a plurality of proteins, and interaction information indicating an interaction between two proteins in the plurality of proteins, to create a combined database.

The therapeutic agent presentation apparatus further includes a searching unit for using the combined database to search for relevance between a mutant protein and a target protein.

The therapeutic agent presentation apparatus further includes a presentation unit for presenting a therapeutic agent acting on a target protein determined to have relevance to a mutant protein, as a therapeutic agent for a disease caused by the mutant protein.

In the therapeutic agent presentation program in the present disclosure, first, a computer is caused to combine a plurality of databases including information of a plurality of proteins, and interaction information indicating an interaction between two proteins in the plurality of proteins, to create a combined database.

In the therapeutic agent presentation program, the computer is further caused to use the combined database and search for relevance between a mutant protein and a target protein.

In the therapeutic agent presentation program, the computer is further caused to present a therapeutic agent acting on a target protein determined to have relevance to a mutant protein, in the therapeutic agent presenting method, as a therapeutic agent for a disease caused by the mutant protein.

In the therapeutic agent presentation method, therapeutic agent presentation apparatus, and therapeutic agent presentation program in the present disclosure, for example, a therapeutic agent having a medicinal effect for a disease is presented not only for a known therapeutic agent, but also for an unknown therapeutic agent, as described below.

Figure 4:
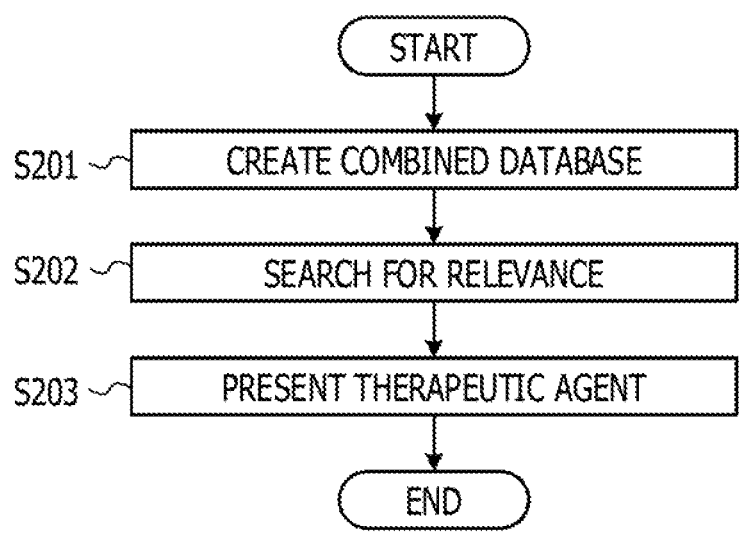
FIG. 4 is a flowchart of an example of a method of presenting a therapeutic agent.
Figure 5:
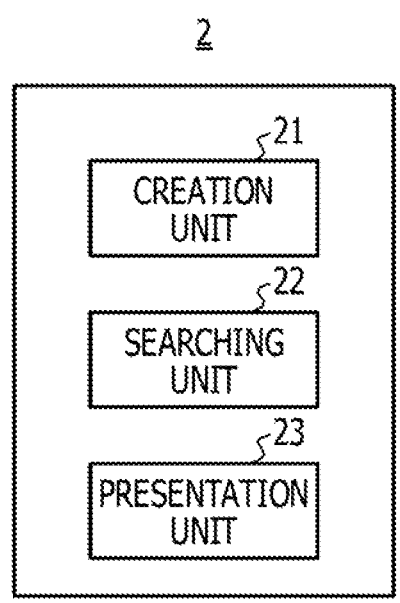
FIG. 5 is a configuration diagram of an example of a therapeutic agent presentation apparatus.

FIG. 4 illustrates a flowchart of an example of a method of presenting a therapeutic agent. FIG. 5 illustrates a configuration diagram of the therapeutic agent presentation apparatus.

Step S201

First, a combined database is created (S201). The creation of the combined database is performed, for example, in a creation unit 21 of a therapeutic agent presentation apparatus 2.

Figure 6A:
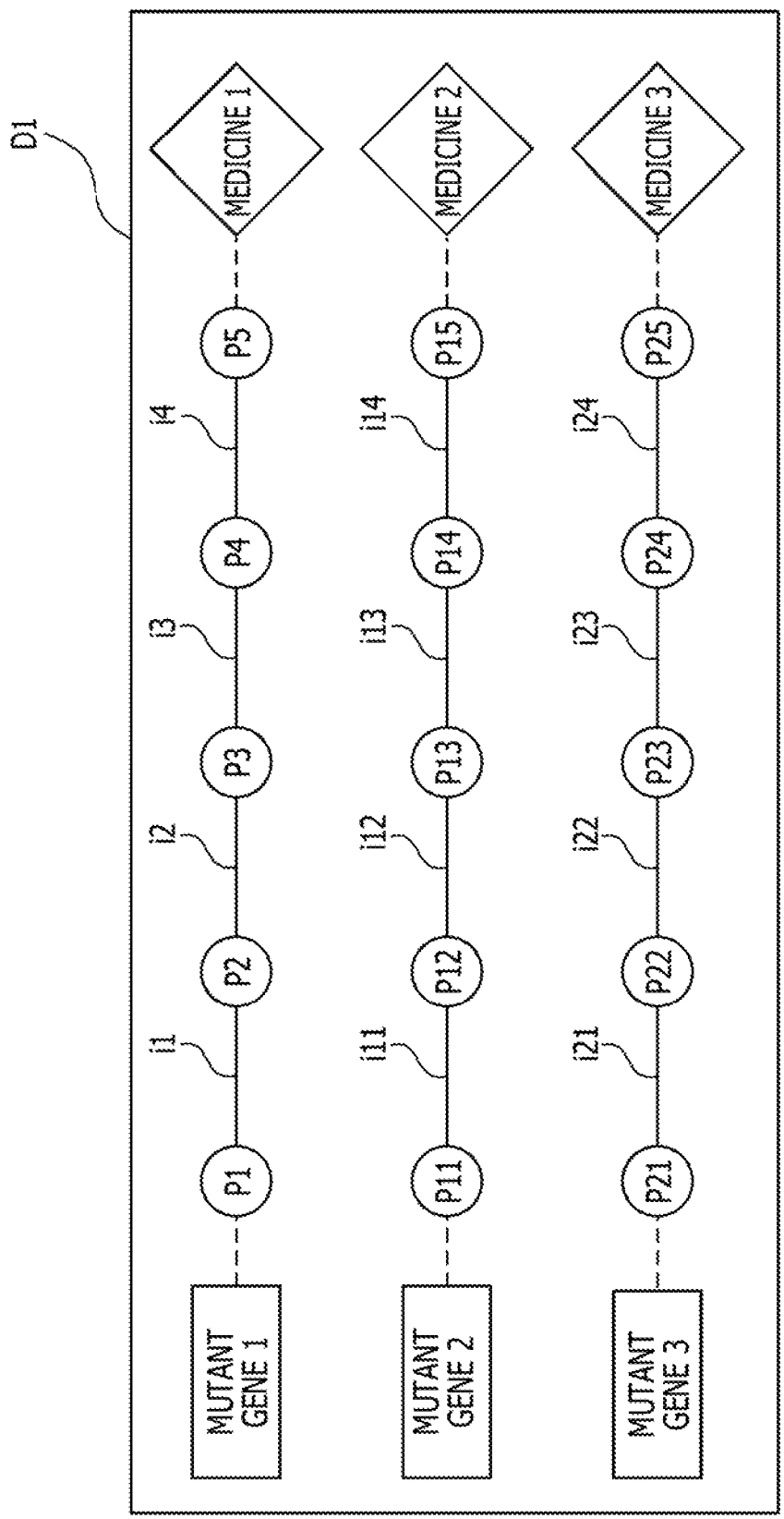
FIG. 6A is an example of a database in which a therapeutic agent and a mutant gene are associated by a reaction pathway.
Figure 6B:
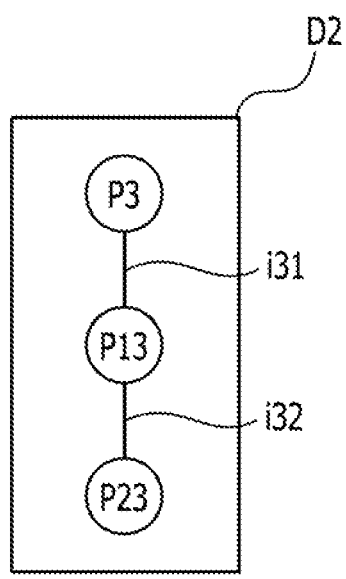
FIG. 6B is an example of a protein-protein interaction database.
Figure 6C:
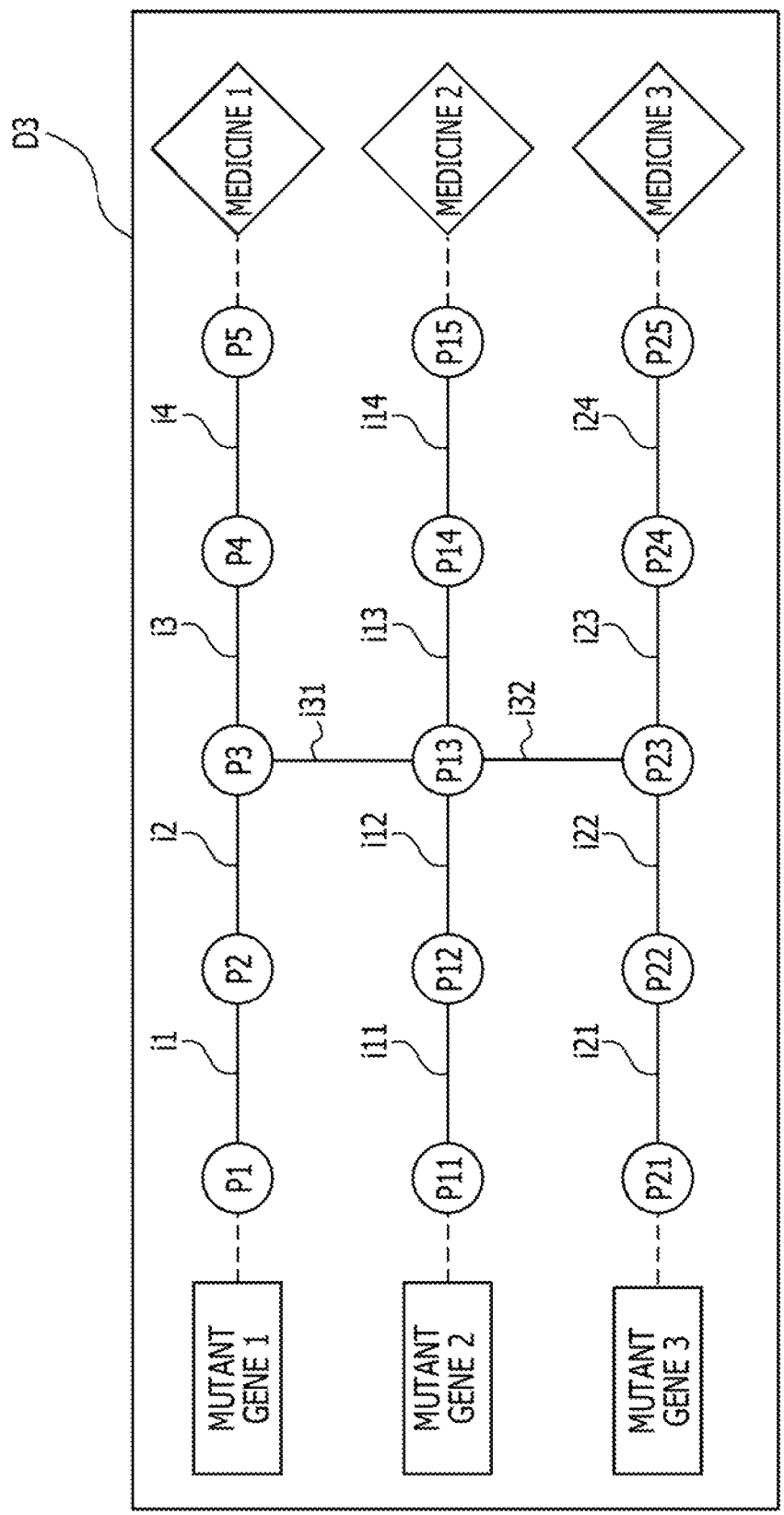
FIG. 6C is an example of a combined database of FIG. 6A and FIG. 6B.

In step S201, for example, a database D1 illustrated in FIG. 6A, and a database D2 illustrated in FIG. 6B are combined to create a combined database D3 illustrated in FIG. 6C.

FIG. 6A illustrates the database D1 in which a therapeutic agent and a mutant gene are associated by a reaction pathway. In FIG. 6A, each of P1 to P5, P11 to P15, and P21 to P25 represents a protein that is an element. In FIG. 6A, each of i1 to i4, i11 to i14, and i21 to i24 represents interaction information indicating an interaction between two proteins (a protein-protein interaction, hereinafter sometimes referred to as a "PPI"), that is individual relevance information constituting a reaction pathway. The protein P1 is a mutant protein generated from a mutant gene 1. The protein P11 is a mutant protein generated from a mutant gene 2. The protein P21 is a mutant protein generated from a mutant gene 3. The protein P5 is a target protein on which a therapeutic agent 1 directly acts. The protein P15 is a target protein on which a therapeutic agent 2 directly acts. The protein P25 is a target protein on which a therapeutic agent 3 directly acts.

FIG. 6B illustrates the database D2 having the proteins P3, P13, P23, and PPIs (i31 and i32).

In the combined database D3 illustrated in FIG. 6C, the database D1 is added to the database D2, so that the following new six types of paths that are not present in the database D1 are generated.

(i) A path between P1 and P15
(ii) A path between P1 and P25
(iii) A path between P11 and P5
(iv) A path between P11 and P25
(v) A path between P21 and P5
(vi) A path between P21 and P15

The number of databases to be combined is not limited to two, and may be three or more.

An example of a database used for combining is illustrated below.

Reactome: a database of reaction pathways
HiNT: a database of protein-protein interactions (PPI database)
INstruct: a database of protein-protein interactions (PPI database)
GuideToPharmacology: a database of therapeutic agents and genes (including information of a target protein on which a therapeutic agent directly acts)

Step S202

Next, the combined database is used to search for relevance between a mutant protein and a target protein (S202). The search for relevance between a mutant protein and a target protein is performed, for example, in the searching unit 22 of a therapeutic agent presentation apparatus 2.

For example, the combined database D3 illustrated in FIG. 6C is used to search for relevance between a mutant protein and a target protein. Examples of the relevance here include, for example, an effect of a target protein on a mutant protein. Strength of such an effect is obtained, for example, by integrating a plurality of pieces of interaction information present in a path between a mutant protein and a target protein.

Figure 7:
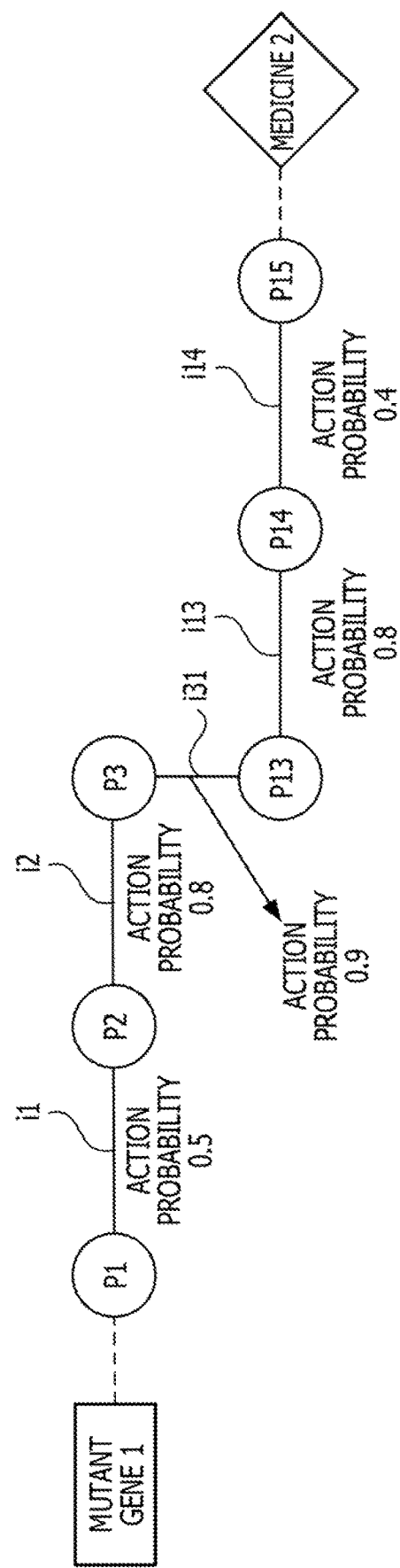
FIG. 7 is a diagram for explaining an example of a method of calculating a path action probability.

For example, as illustrated in FIG. 7, the five PPIs (i1, i2, i31, i13, i14) exist between the protein P1 that is the mutant protein and the protein P15 that is the target protein. For example, when relative strength of each interaction is defined as an action probability, and the action probability is a probability as illustrated in FIG. 7, an action probability of a path between the protein 1 and the protein P15 that is the target protein is calculated as follows.

Path action probability=0.5×0.8×0.9×0.8×0.4=0.1152

Search for relevance between a mutant protein and a target protein may be performed, for example, for all paths present between the mutant protein and the target protein. Search for relevance between a mutant protein and a target protein may be performed for all paths between a specific mutant protein and the target protein.

A method of setting an action probability will be described later.

Step S203

Next, a therapeutic agent acting on a target protein determined to have relevance to a mutant protein is presented as a therapeutic agent for a disease caused by the mutant protein (S203). The presentation is performed, for example, in a presentation unit 23 of the therapeutic agent presentation apparatus 2.

For example, the presentation is performed by displaying path action probabilities calculated for all paths between the specific mutant protein and the target protein as a list. For example, when a therapeutic agent effective for a disease caused by the mutant protein 1 is presented, as illustrated in FIG. 8, a descending list in which individual path action probabilities calculated for all paths between the mutant protein 1 and the target proteins (P1, P15, and P25) are arranged in order from a path action probability having a large numerical value, is created and displayed.

When there is a plurality of paths between a specific mutant protein and a specific target protein, a largest action probability among a plurality of path action probabilities obtained from the plurality of paths may be adopted as a path action probability representing the path action probabilities of the specific mutant protein and the specific target protein (maximum likelihood estimation).

Determination of a target protein having a largest path action probability from the specific mutant protein is equivalent to determination of a target protein having a shortest path from the mutant protein to the target protein by performing the following conversion. For example, determination of a target protein having a large path action probability from the specific mutant protein may be reduced to a shortest path problem, and may be solved by the Dijkstra's algorithm, which is a classical solution for the shortest path problem, for example.

Distance=$C_0$−log (action probability)

Calculation of the invariable $C_0$ is unnecessary for a purpose of determining high or low of the action probability.

Modification Example of Database Combination

A modification example of the database combination in step S201 is illustrated below.

In the description using FIG. 6A to FIG. 6C, the database D1 in which the therapeutic agent and the mutant gene are associated by the reaction pathway is used. In this modification example, a database having information of a mutant protein generated from a mutant gene, a database having information of a target protein on which a therapeutic agent directly acts, and a database having interaction information indicating an interaction between two proteins are used.

Figure 9A:
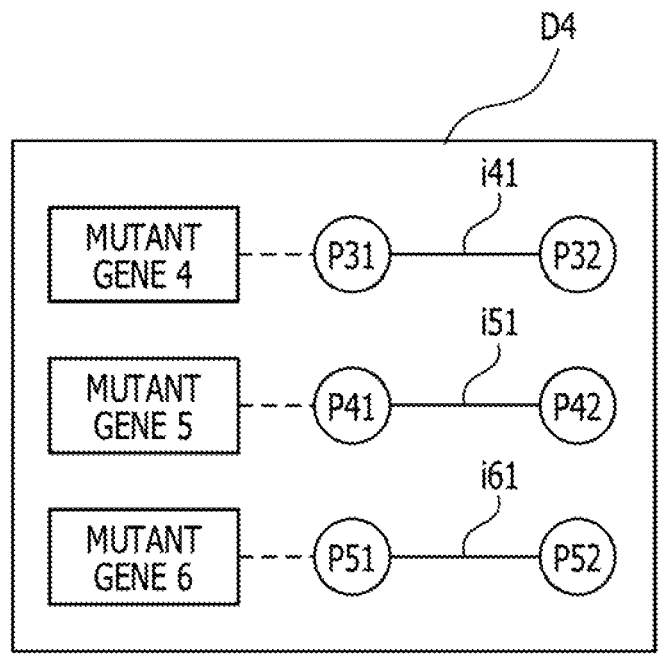
FIG. 9A is an example of a database having information of a mutant protein, information of a protein interacting with the mutant protein, and interaction information between the mutant protein and the protein.

A database illustrated in FIG. 9A is a database D4 having information of a mutant protein generated from a mutant gene, information of a protein interacting with the mutant protein, and interaction information between the mutant protein and the protein. In FIG. 9A, each of P31, P32, P41, P42, P51, and P52 represents a protein. In FIG. 9A, each of i41, i51, and i61 represents interaction information. The protein P31 is a mutant protein generated from a mutant gene 4. The protein P41 is a mutant protein generated from a mutant gene 5. The protein P51 is a mutant protein generated from a mutant gene 6.

Figure 9B:
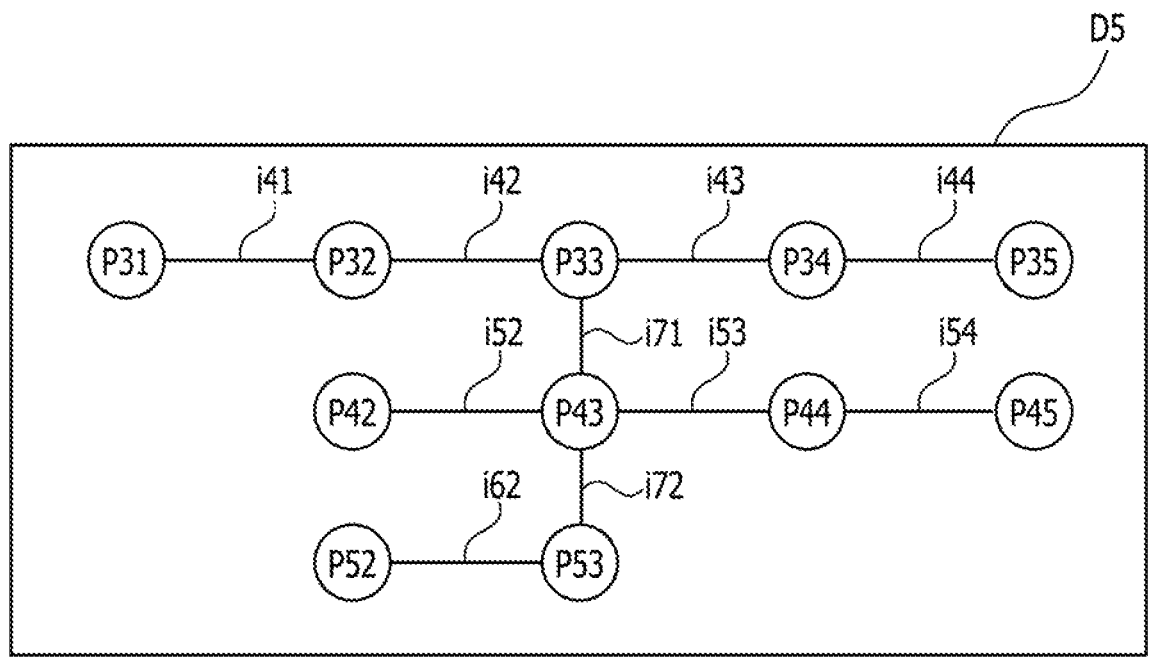
FIG. 9B is an example of a database having information of a protein, and interaction information between two proteins.

A database illustrated in FIG. 9B is a database D5 having information of a protein, and interaction information between two proteins. In FIG. 9B, each of P31, P32, P33, P34, P35, P42, P43, P44, P45, P52, and P53 represents a protein. In FIG. 9B, each of i41, i42, i43, i44, i52, i53, i54, i62, i71, and i72 represents interaction information.

Figure 9C:
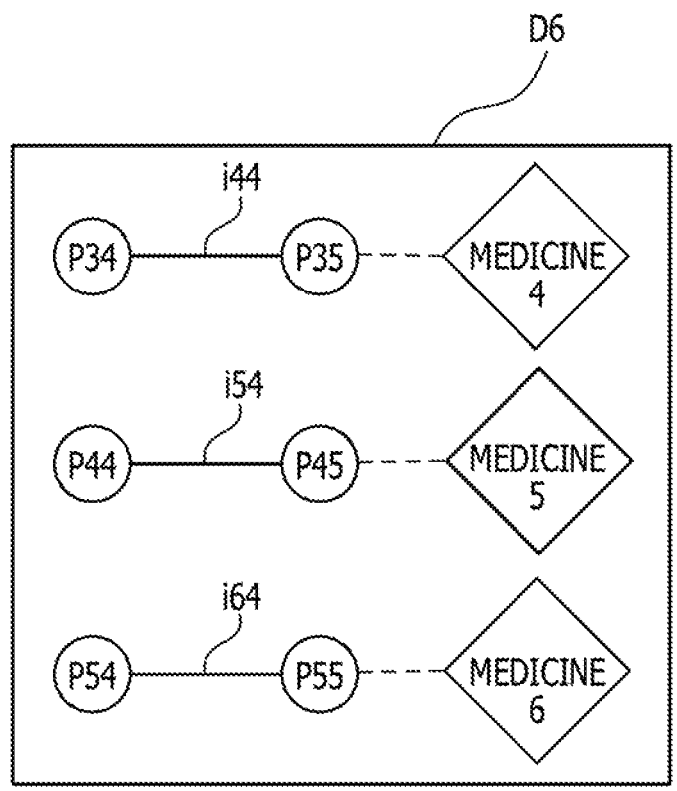
FIG. 9C is an example of a database having information of a target protein, information of a protein interacting with the target protein, and interaction information between the target protein and the protein.

A database illustrated in FIG. 9C is a database D6 having information of a target protein on which a therapeutic agent directly acts, information of a protein interacting with the target protein, and interaction information between the target protein and the protein. In FIG. 9C, each of P34, P35, P44, P45, P54, and P55 represents a protein. In FIG. 9C, each of i44, i54, and i64 represents interaction information.

Figure 9D:
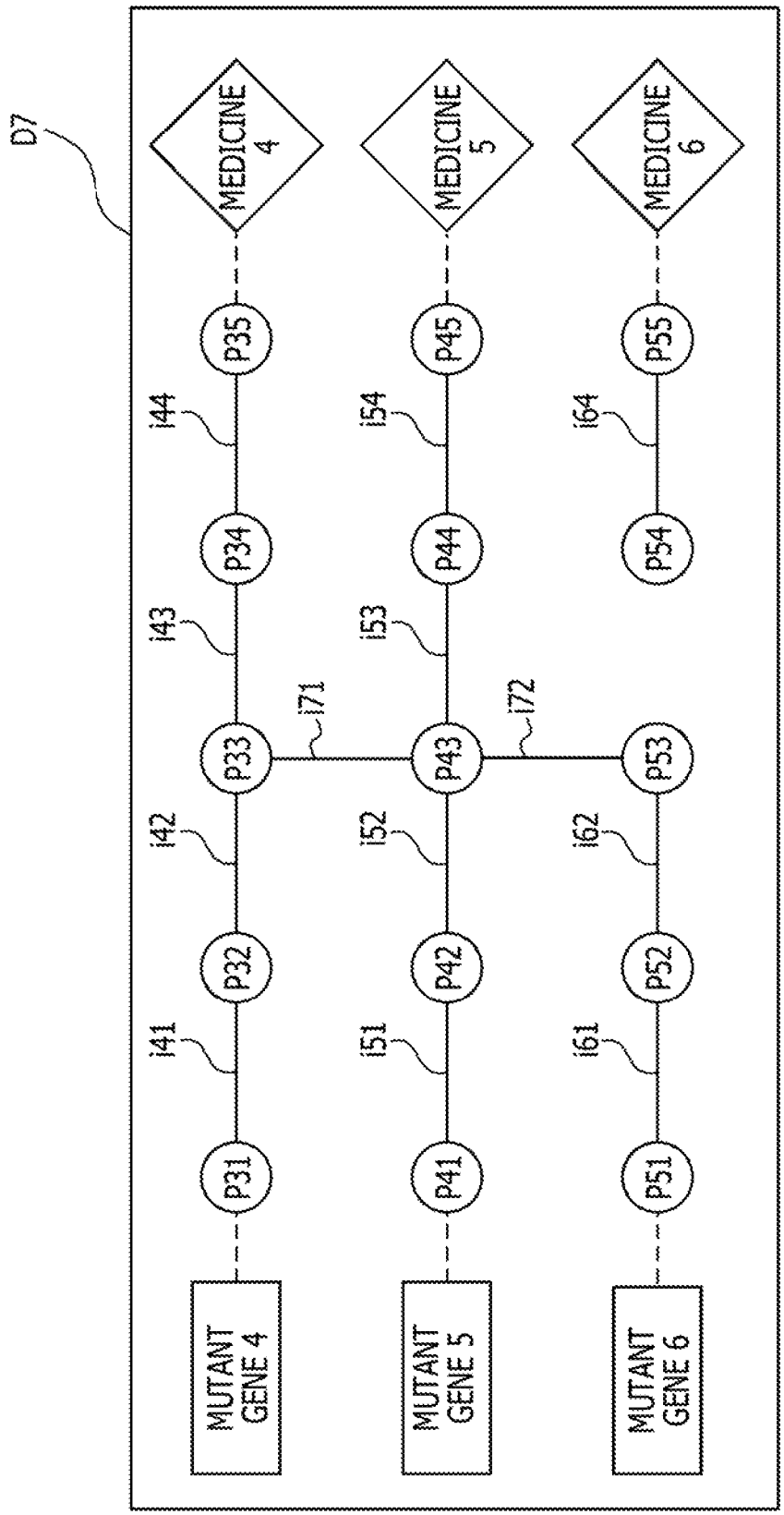
FIG. 9D is an example of a combined database of FIG. 9A, FIG. 9B, and FIG. 9C.

By combining the databases in FIG. 9A, FIG. 9B, and FIG. 9C, a combined database illustrated in FIG. 9D is obtained.

Method of Setting an Action Probability

In step S202, when the combined database is used to search for relevance between a mutant protein and a target protein, for example, relative strength of an interaction between the mutant protein and the target protein is obtained, from a plurality of pieces of interaction information present in a path between the mutant protein and the target protein. At this time, a path action probability is calculated from a product of action probabilities that are relative strength of individual interactions (individual interaction information).

The individual action probability at that time may be set, for example, by machine learning according to Bayesian estimation. An example of a method thereof will be described below.

FIG. 10 is a flowchart for explaining an example of setting an action probability.

Step S301 (Creation of a Combined Database)

Figure 11A:
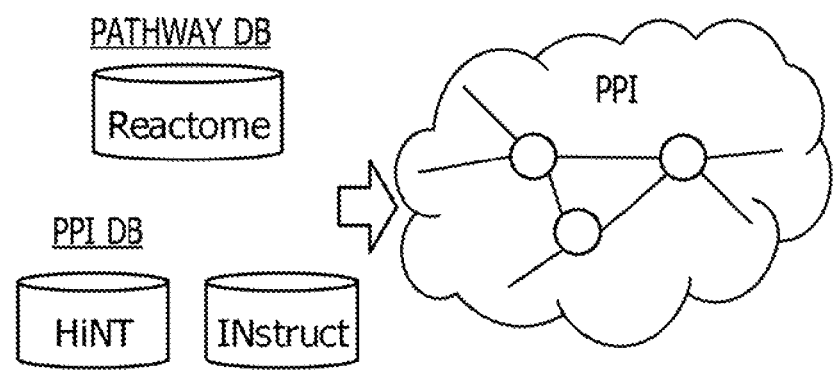
FIG. 11A is a diagram for explaining an example of a method of setting an action probability (1)

First, as a preparation stage, a plurality of databases is combined to create a combined database (S301). FIG. 11A is a conceptual diagram of a state in which the databases are combined. In FIG. 11A, Reactome is used as the reaction pathway database (DB), and HINT and INstruct are used as the PPI databases.

Structure of the combined database is, for example, graph structure in which a protein is a node, and a protein-protein interaction (PPI) is an edge, and as for a size of the graph structure, for example, the number of nodes is several tens of thousands, and the number of edges is several hundreds of thousands.

Step S302 [Preparation Stage of Learning (1)]

As a preparation stage for learning an action probability (1), an initial value of an action probability is set for a protein-protein interaction (PPI) in the combined database (S302).

In this case, real values of the respective edges may be greatly different from each other, and thus it is risky to provide a single initial value. When estimating an action probability, since there is large variation in medicinal effect data for each medicine or case to be used as training data, accuracy of the estimation is demanded to be controlled in accordance with a size of the training data.

Figure 11B:
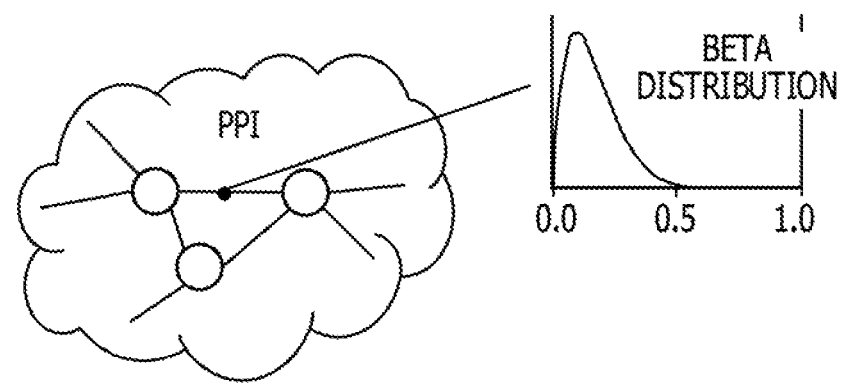
FIG. 11B is a diagram for explaining the example of the method for setting an action probability (2)

Thus, it is preferable to provide probability distribution of an estimated value instead of providing a single estimated value as an action probability. Since an action itself is described with the Bernoulli distribution indicating presence or absence, convenience is enhanced when, as probability distribution indicating an action probability, beta distribution that is conjugate prior distribution of the Bernoulli distribution is adopted (FIG. 11B). FIG. 11B is a conceptual diagram illustrating a state in which the beta distribution is provided as an initial value of an action probability to a protein-protein interaction (PPI).

Thus, the beta distribution Be ($\alpha_{PPI}$ and $\beta_{PPI}$) is assigned to the action probability of the PPI as prior distribution. $\alpha_{PPI}$ and $\beta_{PPI}$ are parameters of the distribution, and are set such that respective expected values become a low value such as 0.1. A probability density function thereof is represented by the following equation [however, B(,) is a beta function].

$$f(x; \alpha_{PPI}, \beta_{PPI}) = \frac{x^{\alpha_{PPI}-1}(1-x)^{\beta_{PPI}-1}}{B(\alpha_{PPI}, \beta_{PPI})}$$

Step S303 [Preparation Stage of Learning (2)]

Next, as a preparation stage of learning an action probability (2), prior distribution of an action probability of a PPI in a known reaction pathway is set. This is because a known reaction pathway may be a mechanism of an effective medicinal effect, and thus has high utility, and it is preferable to provide high prior distribution to an action probability of a PPI in the known reaction pathway. The known reaction pathway is information recorded in Reactome, that is the pathway DB.

For each PPI appearing in the known reaction pathway, an action probability thereof is subjected to the Bayesian update with a probability that is high to some extent and the number of trials that is appropriately set (S303). When the prior distribution is represented by a probability density function $f_{prior}$ (x; $\alpha$, $\beta$) of the beta distribution, a density function of a posterior probability that is subjected to trials with a success rate r (for example, r=0.99), and the number of trials n (for example, n=0.1), and to the Bayesian update is calculated by the Bayes theorem and according to the following equation $f_{posterior}$ (x; $\alpha$, $\beta$). Since this is solved in a closed form, calculations is easy. $\alpha$ represents the number of times for which a medicinal effect is recognized, and β represents the number of times for which the medicinal effect is not recognized.

$$f_{posterior}(x; \alpha, \beta) = \frac{x^{nr}(1-x)^{n(1-r)} \cdot f_{prior}(x; \alpha, \beta)}{\int_0^1 x^{nr}(1-x)^{n(1-r)} \cdot f_{prior}(x; \alpha, \beta)dx}$$

Since a PPI is duplicate among a plurality of reaction pathways in some cases, the Bayesian update may be performed multiple times for a certain PPI.

Step S304 [Sub Step (Application of Bayesian Update to a Similar PPI)]

A PPI similar to a PPI in a reaction pathway is expected to behave similarly to the PPI in the reaction pathway. When the PPI is a PPI that is not included in learning data, the PPI may serve as a clue for estimating an unknown medicinal effect. Examples of a similar PPI include, for example, a PPI with the same interaction between domains as that of the PPI in the reaction pathway. A hypothesis that "PPIs having the same interaction between domains are similar to each other" is applied. For determination of similar PPIs, for example, information of an interaction between domains for proteins in the database INstruct is used.

When the Bayesian update by the PPI in the reaction pathway is performed, a similar PPI to that PPI is subjected to the Bayesian update weakly (=with the number of trials reduced) (S304). For example, trials are performed with the success rate r (for example, r=0.99), and the number of trials n (for example, n=0.001). In this way, knowledge is diverted.

Figure 11C:
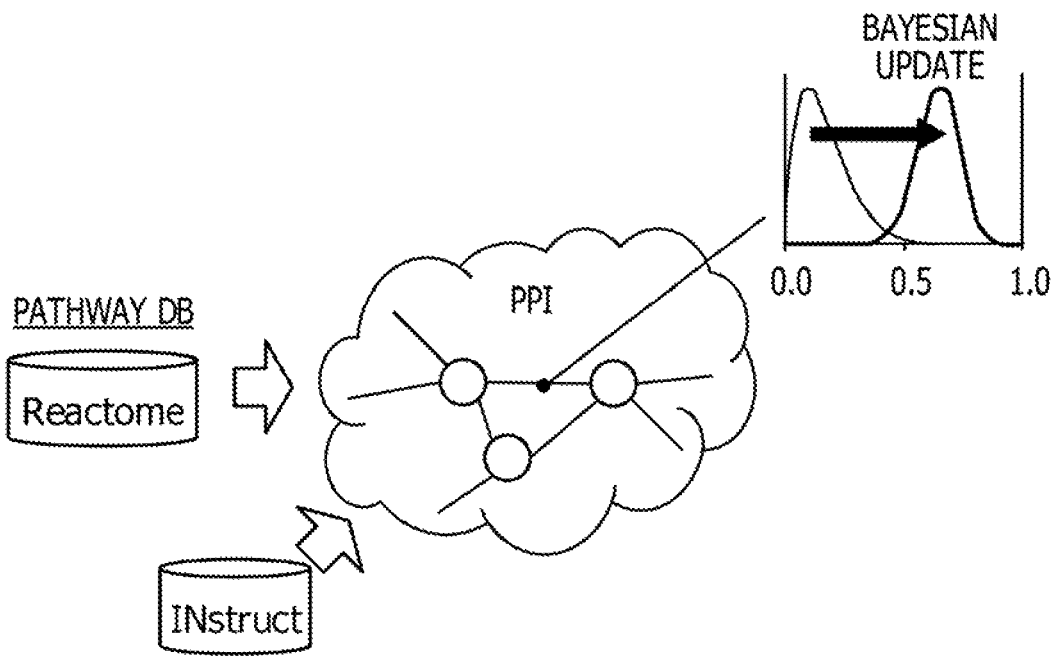
FIG. 11C is a diagram for explaining the example of the method for setting an action probability (3)

FIG. 11C is a conceptual diagram illustrating a state in which an action probability of a PPI appearing in a known reaction pathway is subjected to the Bayesian update.

Step S305 (Learning Stage)

Learning is performed by using learning data, as a learning stage (S305).

Figure 11D:
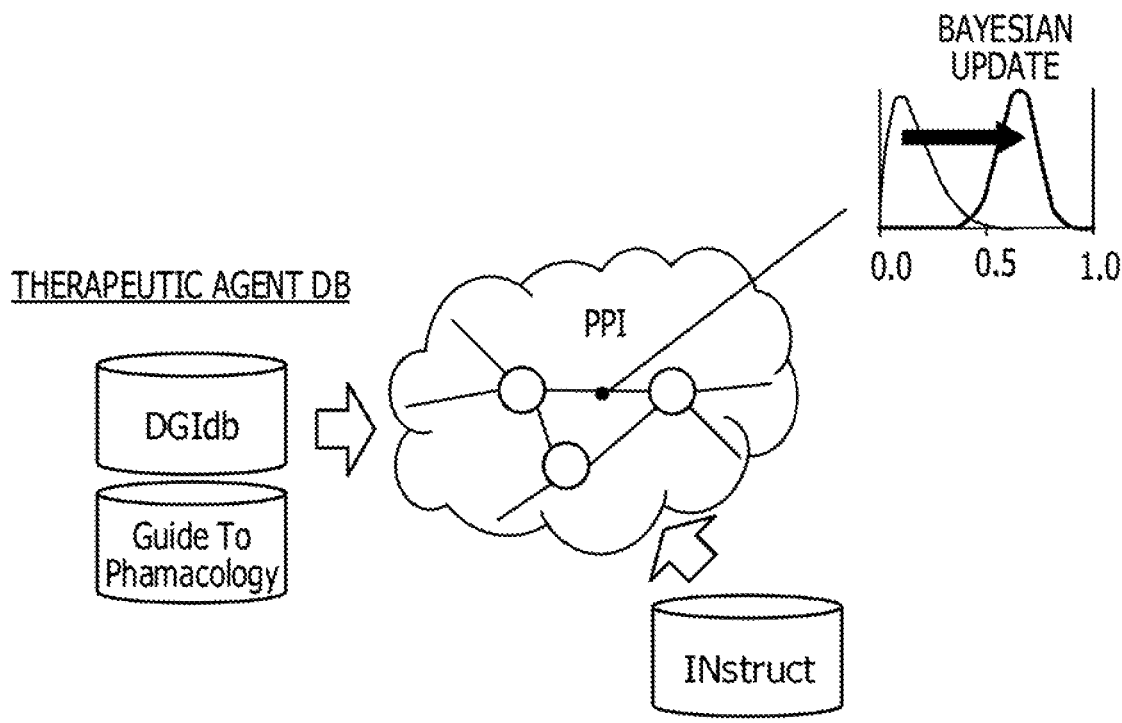
FIG. 11D is a diagram for explaining the example of the method for setting an action probability (4)
Figure 12:
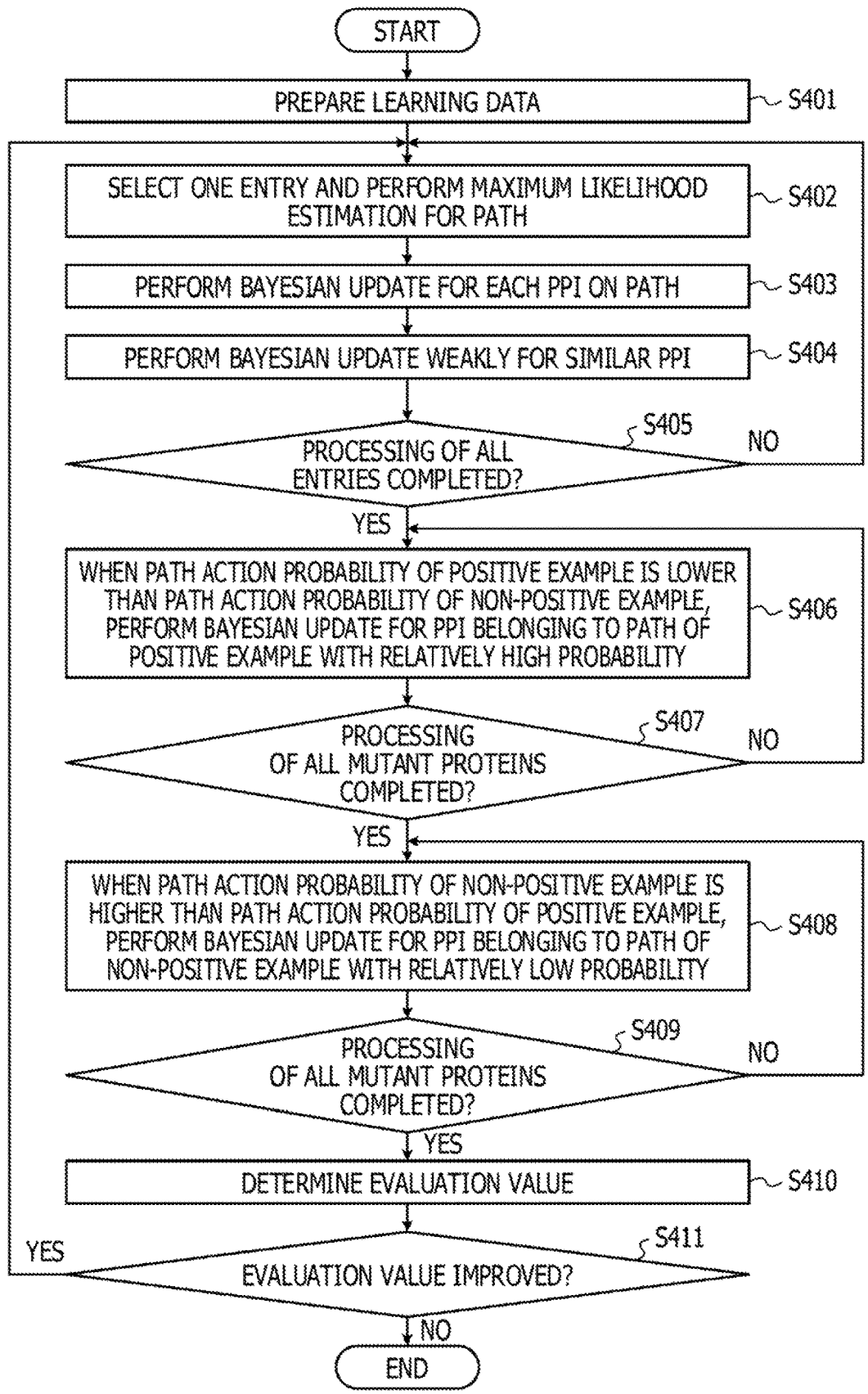
FIG. 12 is a flowchart for explaining an example of a learning method.

The learning is performed, for example, in the following manner. FIG. 11D is a conceptual diagram illustrating a state in which the learning is performed using learning data according to the following method. FIG. 12 is a flowchart of the following learning. An example of the learning using the learning data will be described below with reference to the flowchart in FIG. 12.

Step S401

By using a database DGIdb and a database GuideToPharmacology, learning data including a pair of a mutant protein having a known medicinal effect and a target protein is prepared (S401).

Step S402

Next, one entry is selected from the learning data, and maximum likelihood estimation is performed for a path between a mutant protein and a target protein (S402). This is equivalent to solving a shortest path problem.

Step S403

The Bayesian update is performed for a PPI on the path subjected to the maximum likelihood estimation, with a probability that is high to some extent, and the number of trials that is appropriately set (S403). For example, trials are performed with the success rate r (for example, r=0.99), and the number of trials n (for example, n=0.3).

Step S404

Similarly to step S304, the Bayesian update is weakly performed for a similar PPI, as well (S404).

Step S405

Step S402 to Step S404 are repeated for all entries (S405).

Step S406

A certain mutant protein is selected, and path action probabilities to all target proteins are enumerated, and when a path action probability of a positive example (target protein present in the learning data) is lower than a path action probability of a non-positive example, a PPI belonging to a path of the positive example is subjected to the Bayesian update with a relatively high probability (S406). For example, trials are performed with the success rate r (for example, r=0.99), and the number of trials n (for example, n=0.3).

Step S407

Step S406 is repeated for all mutant proteins (S407).

Step S408

A certain mutant protein is selected, and path action probabilities to all target proteins are enumerated, and when a path action probability of a non-positive example is higher than a path action probability of a positive example, a PPI belonging to a path of the non-positive example is subjected to the Bayesian update with a relatively low probability (S408). For example, trials are performed with the success rate r (for example, r=0.10), and the number of trials n (for example, n=0.3).

Step S409

Step S409 is repeated for all mutant proteins (S409).

Step S410

An evaluation value (for example, an average of Recall@k to be described later) is determined (S410).

Step S411

While the evaluation is being improved, step S402 to step S410 are repeated.

Recall@k is a performance evaluation index indicating a percentage of correct answers that are included in the upper k pieces, of all correct answers in data. A larger value means that the evaluation is accurate.

A reason why the action probability is repeatedly and gradually changed will be described.

Figure 13:
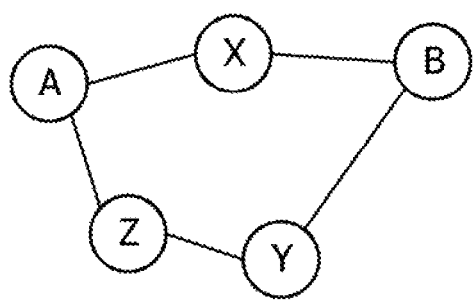
FIG. 13 is a diagram for explaining an example of a reason why an action probability is changed repeatedly and gradually.

For example, when there are PPIs as illustrated in FIG. 13, and an entry of the learning data from a mutant protein A to a target protein B appears, a path A-X-B is selected first.

At this time, when a true path is A-Z-Y-B, the path selected first is false. If a too high probability is assigned to a PPI of the path A-X-B first, the path A-Z-Y-B will never be traced.

If the change in probability is slight, there remains a chance that respective PPIs of A-Z, Z-Y, and Y-B are learned with a high probability from other learning data. This means that a state of falling into a wrong local solution and being unable to escape is avoided.

Search for a Friendship

The relevance searching method, the relevance searching apparatus, and the relevance searching program may also be used to search for a friendship that may not be searched for from an existing single database.

Today, there are many social networking services (hereinafter, sometimes referred to as "SNSs") on the Internet. They have functions of performing friendship search independently in some cases.

However, it is not possible to perform friendship search across the SNSs.

By using an example of the relevance searching method, the relevance searching apparatus, and the relevance searching program in the present disclosure, it is possible to search for a friendship that may not be searched for from an existing single database. The method will be described below.

In the following description, when the relevance searching method is used for searching a friendship, the relevance searching method is referred to as a friend searching method. When the relevance searching apparatus is used for searching a friendship, the relevance searching apparatus is referred to as a friend searching apparatus. When the relevance searching program is used for searching a friendship, the relevance searching program is referred to as a friend searching program.

In the friend searching method in the present disclosure, first, a plurality of databases each including information of a plurality of persons, and relevance information indicating direct relevance between two persons in the plurality of persons, is combined to create a combined database.

In the friend searching method, the combined database is further used to search for relevance between two persons that do not have direct relevance.

In the friend searching method, for example, relevance between two persons that are determined to have relevance but do not have direct relevance, is further presented.

In the friend searching apparatus in the present disclosure, a creation unit is included for combining a plurality of databases each including information of a plurality of persons, and relevance information indicating direct relevance between two persons in the plurality of persons, to create a combined database.

The friend searching apparatus further includes a searching unit that uses the combined database to search for relevance between two persons that do not have direct relevance.

The friend searching apparatus, for example, further includes a presentation unit for presenting relevance between two persons that are determined to have relevance but do not have direct relevance.

The friend searching program in the present disclosure causes a computer to combine a plurality of databases each including information of a plurality of persons and relevance information indicating direct relevance between two persons in the plurality of persons, to create a combined database.

In the friend searching program, the combined database is further used to search for relevance between two persons that do not have direct relevance.

In the friend searching program, for example, relevance between two persons that are determined to have relevance but do not have direct relevance is further presented.

Structure of the combined database is graph structure in which, for example, personal information is a node, and relevance information is an edge.

The relevance information is, for example, information indicating strength of direct relevance between two persons, and examples include, for example, a common hobby, the number of common friends, the number of conversations in SNSs, and the like.

In the friend searching method, the friend searching apparatus, and the friend searching program, for example, relevance between elements that may not be searched for from only a single database is searched for, as follows.

Figure 14:
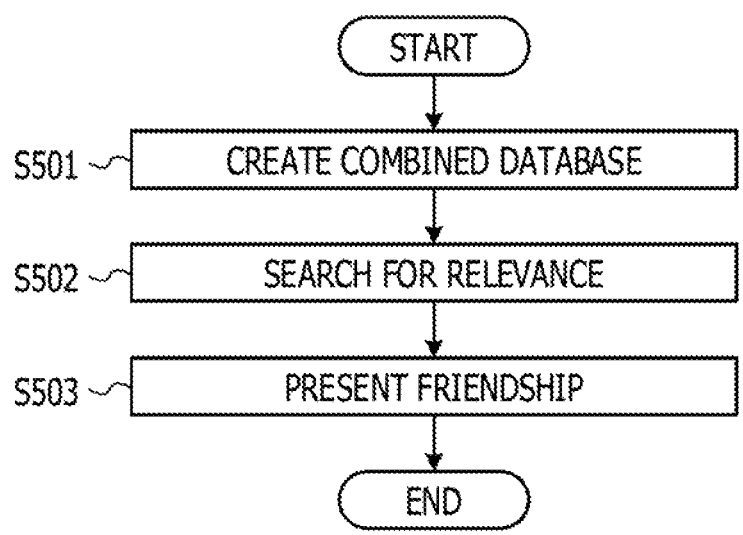
FIG. 14 is a flowchart of an example of a method of searching for a friendship.
Figure 15:
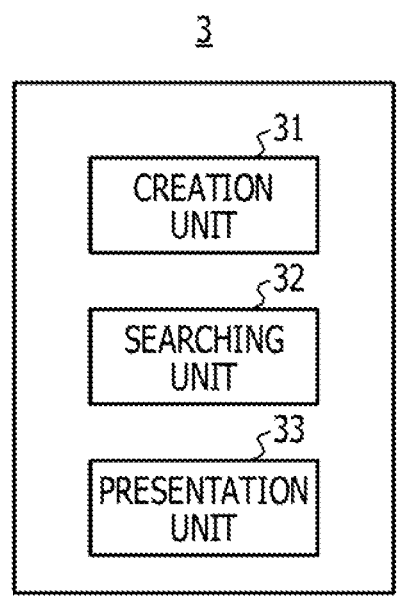
FIG. 15 is a configuration diagram of an example of a friend searching apparatus.

FIG. 14 illustrates a flowchart of an example of a method of searching for a friendship. FIG. 15 illustrates a configuration diagram of a friend searching apparatus 3.

Step S501

First, a combined database is created (S501). The creation of the combined database is performed, for example, in the creation unit 31 of the friend searching apparatus 3.

Figure 16A:
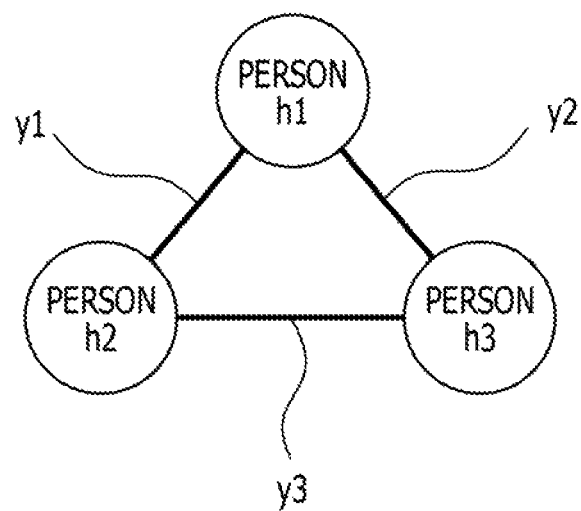
FIG. 16A is an example of graph structure of a first database.
Figure 16B:
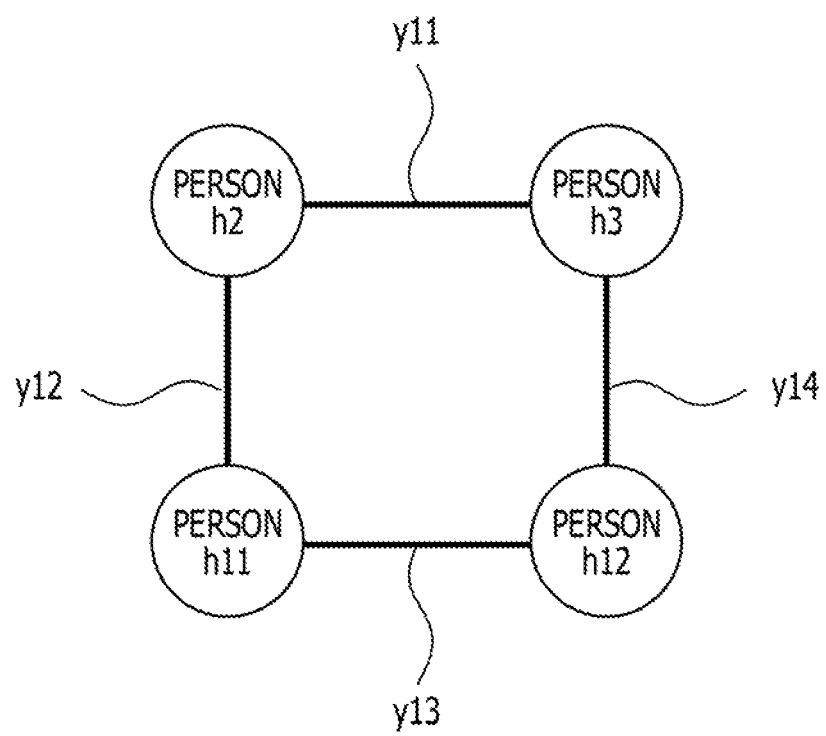
FIG. 16B is an example of graph structure of a second database.
Figure 16C:
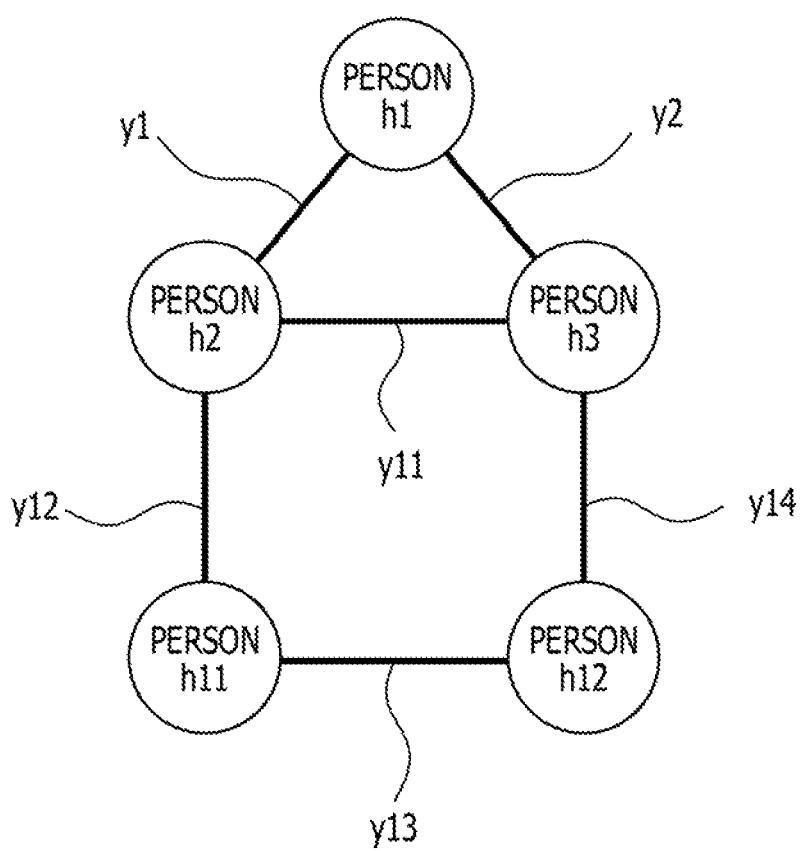

In step S501, for example, a first database having graph structure illustrated in FIG. 16A and a second database having graph structure illustrated in FIG. 16B are combined to create a combined database having graph structure illustrated in FIG. 16C.

The first database has personal information h1 to personal information h3, and relevance information y1 to relevance information y3 each indicating direct relevance between two persons. The graph structure illustrated in FIG. 16A is graph structure in which each of the personal information h1 to the personal information h3 is a node, and each of the relevance information y1 to the relevance information y3 is an edge.

The second database has the personal information h2, the personal information h3, personal information h11, and personal information h12, and relevance information y11 to relevance information y14 each indicating direct relevance between two persons. The graph structure illustrated in FIG. 16B is graph structure in which each of the personal information h2, the personal information h3, the personal information h11, and the personal information h12 is a node, and each of the relevance information y11 to the relevance information y14 each indicating the direct relevance between two persons is an edge.

In the creation of the combined database, for example, duplicate pieces of personal information are integrated into one piece of personal information.

The combined database in which the first database and the second database are combined, as illustrated in FIG. 16C, has the personal information h1, the personal information h2, the personal information h3, the personal information h11, and the personal information h12, and the relevance information y1, the relevance information y2, and the relevance information y11 to the relevance information y14 each indicating the direct relevance between the two persons. The graph structure illustrated in FIG. 16C is graph structure in which each of the personal information h1, the personal information h2, the personal information h3, the personal information h11, and the personal information h12 is a node, and each of the relevance information y1, the relevance information y2, and the relevance information y11 to the relevance information y14 is an edge.

When the combined database is created, and there is relevance information indicating direct relevance between two persons (for example, when there are the relevance information y3 and the relevance information y11 that are different from each other between the personal information h2 and the personal information h3), the combined database may be created using any of the pieces of relevance information.

The number of databases to be combined is not limited to two, and may be three or more.

Step S502

Next, the combined database is used to search for relevance between two persons that do not have direct relevance (S502). The search for the relevance between the two persons is performed, for example, in a searching unit 32 of the friend searching apparatus 3.

For example, the combined database having the graph structure illustrated in FIG. 16C is used to search for relevance between the personal information h1 and the personal information h11, that do not have direct relevance. This relevance is relevance that is not found in the first database alone having the graph structure illustrated in FIG. 16A, or in the second database alone having the graph structure illustrated in FIG. 16B. Strength of the relevance between the personal information h1 and the personal information h11 is calculated, for example, by totaling a plurality of pieces of relevance information present in one path between the personal information h1 and the personal information h11.

Step S503

Next, relevance between two persons that are determined to have relevance but do not have direct relevance is presented (S503). The presentation is performed, for example, in a presentation unit 33 of the friend searching apparatus 3.

For example, the presentation of the relevance include, for example, presentation of a common hobby, the number of common friends, and the like.

The program in the present disclosure may be created by using various known program languages depending on a configuration a computer system used, a type, a version, and the like of an operating system.

The program in the present disclosure may be recorded on a recording medium such as a built-in hard disk, or an external hard disk, or may be recorded on a recording medium such as a compact disc read-only memory (CD-ROM), a digital versatile disk read-only memory (DVD-ROM), a magneto-optical (MO) disk, or a Universal Serial Bus (USB) memory (USB flash drive). When the program is to be recorded on a recording medium such as a CD-ROM, a DVD-ROM, an MO disk, or a USB memory, it is possible to directly use the program, or to use the program by installing the program on a hard disk, through a recording medium reading apparatus included in a computer system, as appropriate, at any time. It is also possible to record the program in an external storage area (other computer or the like) accessible from the computer system through an information communication network, and use the program directly or by installing the program in a hard disk, through the information communication network from the external storage area, as appropriate, at any time.

The programs may be divided and recorded on a plurality of recording media for each arbitrary process.

The program in the present disclosure is recorded in, for example, a recording medium that is readable by the computer in the present disclosure.

The computer readable recording medium is not particularly limited, and may be appropriately selected depending on a purpose, and examples thereof include, for example, a built-in hard disk, an external hard disk, a CD-ROM, a DVD-ROM, an MO disk, a USB memory, and the like.

The recording medium may be a plurality of recording media in which programs are divided and recorded for each arbitrary process.

Figure 17:
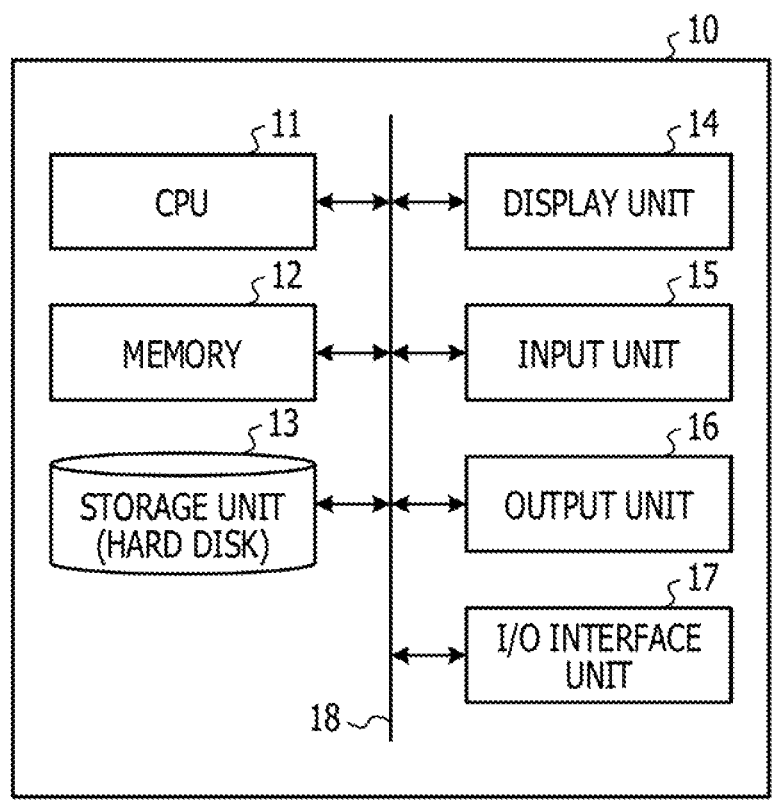
FIG. 17 is a hardware configuration diagram of an example of a relevance searching apparatus in the present disclosure.

FIG. 17 illustrates an example of the relevance searching apparatus in the present disclosure.

A relevance searching apparatus 10 is configured, for example, by coupling a central processing unit (CPU) 11, a memory 12, a storage unit 13, a display unit 14, an input unit 15, an output unit 16, an I/O interface unit 17, and the like, via a system bus 18.

The central processing unit (CPU) 11 performs calculation (four arithmetic operations, a comparison operation, and the like), operation control of hardware and software, and the like.

The memory 12 includes memories such as a random-access memory (RAM), and a read-only memory (ROM). The RAM stores an operating system (OS), an application program, and the like, read from the ROM and the storage unit 13, and functions as a main memory and a work area of the CPU 11.

The storage unit 13 is a device for storing various programs and data, and is a hard disk, for example. The storage unit 13 stores a program to be executed by the CPU 11, data demanded for the program execution, the OS, and the like.

The program is stored in the storage unit 13, loaded into the RAM (main memory) of the memory 12, and executed by the CPU 11.

The display unit 14 is a display apparatus, and is, for example, a display device such as a cathode-ray tube (CRT) monitor, or a liquid crystal panel.

The input unit 15 is an input device for various types of data, and is, for example, a keyboard, a pointing device (for example, a mouse, or the like), or the like.

The output unit 16 is an output device for various types of data, and is, for example, a printer.

The I/O interface unit 17 is an interface for coupling various external devices. The I/O interface unit 17 enables, for example, input and output of data in a CD-ROM, a DVD-ROM, an MO disk, a USB memory, and the like.

Figure 18:
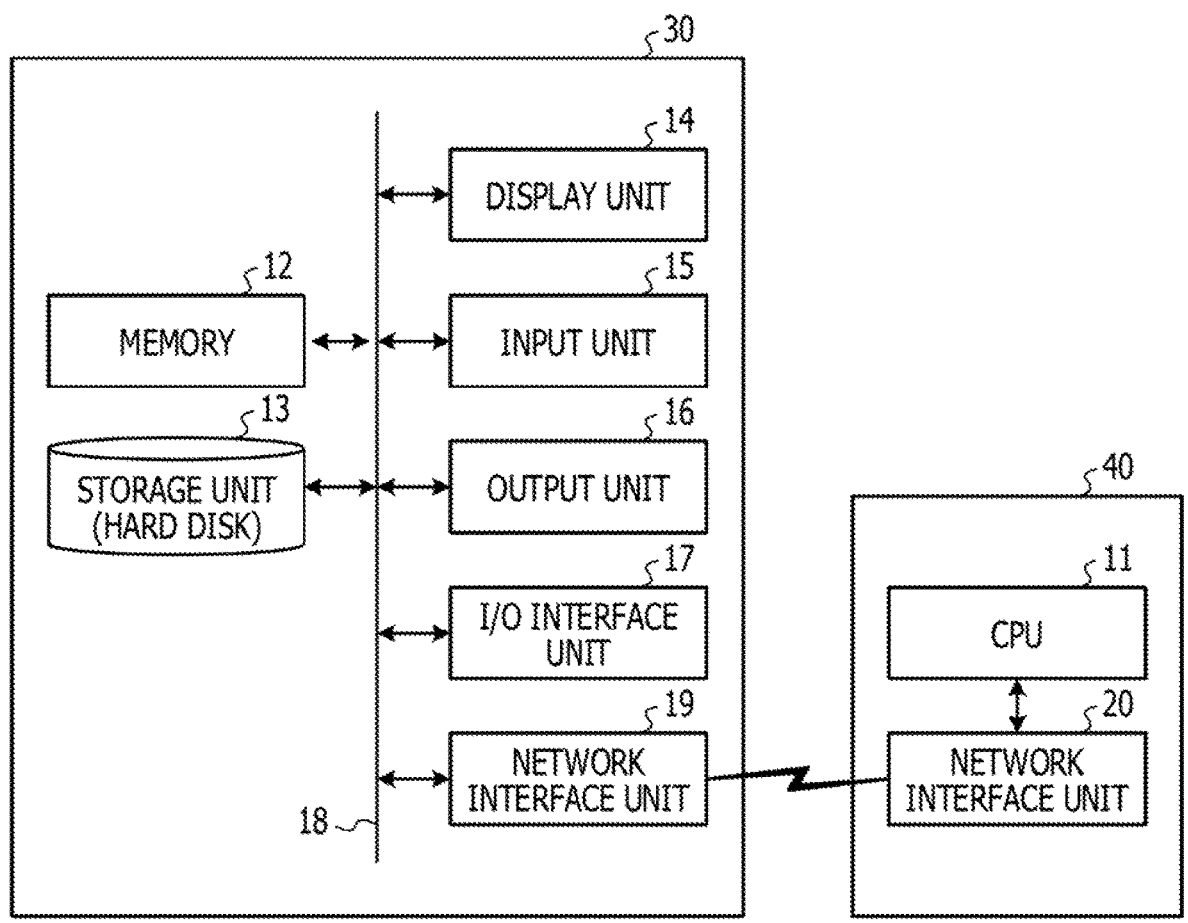
FIG. 18 is a hardware configuration diagram of another example of the relevance searching apparatus in the present disclosure.

FIG. 18 illustrates another example of the relevance searching apparatus in the present disclosure.

The example in FIG. 18 is a configuration example of a cloud type, and the CPU 11 is independent of the storage unit 13, and the like. In the configuration example, a computer 30 housing the storage unit 13, and the like, and a computer 40 housing the CPU 11 are coupled via the network interface units 19 and 20.

The network interface units 19 and 20 are each hardware for performing communication by using the Internet.

Figure 19:
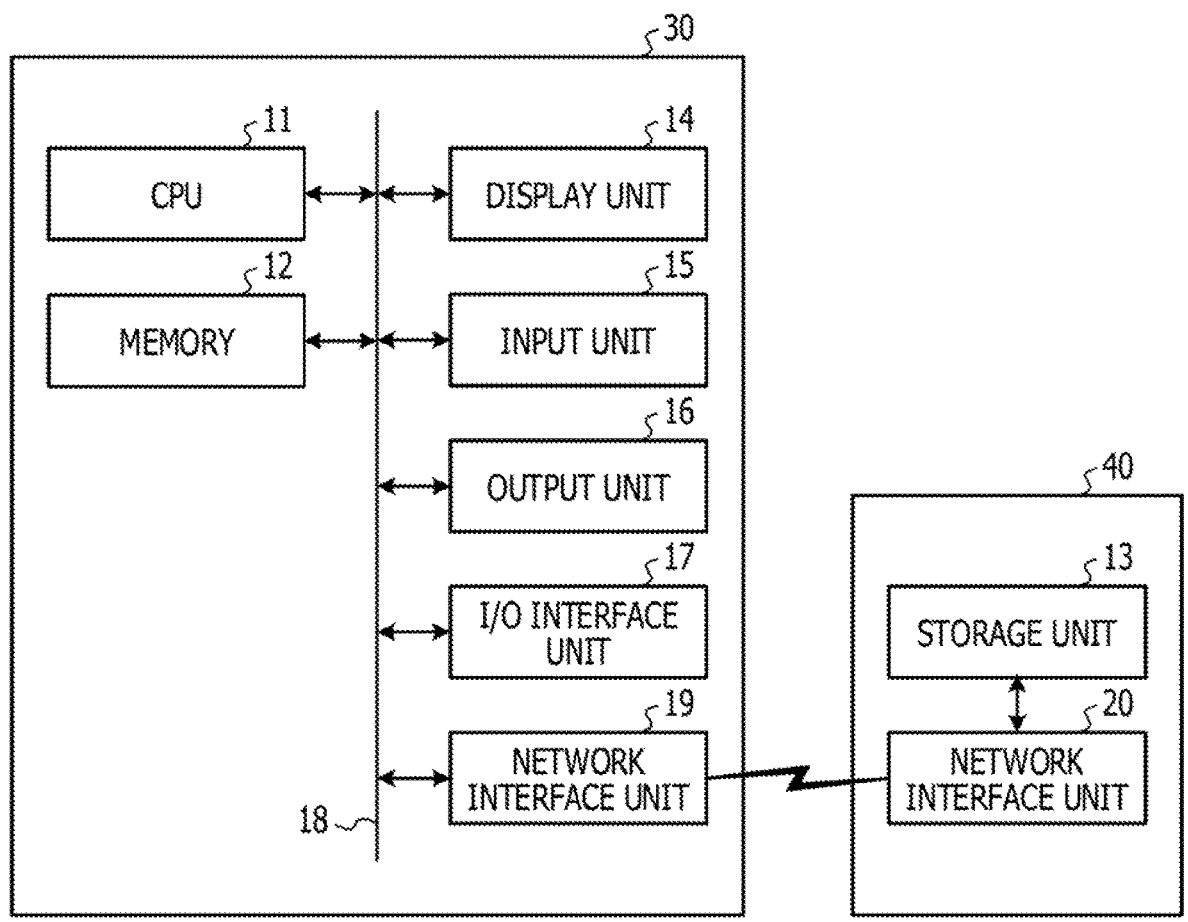
FIG. 19 is a hardware configuration diagram of another example of the relevance searching apparatus in the present disclosure.

FIG. 19 illustrates another example of the relevance searching apparatus in the present disclosure.

The example in FIG. 19 is a configuration example of a cloud type, and the storage unit 13 is independent of the CPU 11, and the like. In the configuration example, the computer 30 housing the CPU 11, and the like, and the computer 40 housing the storage unit 13 are coupled via the network interface units 19 and 20.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A relevance searching method performed by a computer, the relevance searching method comprising:
   generating a combined database by combining a plurality of databases each including a plurality of elements and relevance information indicating direct relevance between two elements in the plurality of elements; and
   searching for relevance between two elements that do not have direct relevance by using the combined database,
   wherein the plurality of elements is a plurality of pieces of protein information, the relevance information is interaction information indicating an interaction between two proteins in a plurality of proteins, the plurality of databases includes a database having information of the mutant protein generated from a mutant gene, and information of the target protein on which a therapeutic agent directly acts, and searching for the relevance is searching for relevance between a mutant protein and a target protein,
   wherein each piece of the interaction information in the combined database is an action probability indicating relative strength of an interaction, and the action probability is set by machine learning.

2. The relevance searching method according to claim 1, wherein the combined database has graph structure in which the element is a node, and the relevance information is an edge.

3. The relevance searching method according to claim 1, wherein relevance between two elements that are determined to have relevance but do not have direct relevance is presented.

4. The relevance searching method according to claim 1, wherein the plurality of elements is a plurality of pieces of protein information, the relevance information is interaction information indicating an interaction between two proteins in the plurality of proteins, the plurality of databases includes a database having information of the mutant protein generated from a mutant gene, and a database having information of the target protein on which a therapeutic agent directly acts, and searching for the relevance is searching for relevance between a mutant protein and a target protein.

5. The relevance searching method according to claim 1, wherein in the machine learning, learning is performed by using learning data, after an initial value of the action probability is set as beta distribution, and an initial value of an action probability of interaction information that is a target provided with a high action probability is subjected to Bayesian update.

6. The relevance searching method according to claim 5, wherein in the machine learning, for an initial value of an action probability of interaction information analogous to the interaction information that is a target provided with a high action probability, Bayesian update is performed that is weaker than the Bayesian update of the initial value of the action probability of the interaction information that is a target provided with a high action probability.

7. The relevance searching method according to claim 5, wherein the learning data is data of a pair of a mutant protein having a medicinal effect and a target protein.

8. A relevance searching apparatus, comprising:
   a memory; and
   a processor coupled to the memory and the processor configured to:
      generate a combined database by combining a plurality of databases each including a plurality of elements and relevance information indicating direct relevance between two elements in the plurality of elements; and
      search for relevance between two elements that do not have direct relevance by using the combined database,
   wherein the plurality of elements is a plurality of pieces of protein information, the relevance information is interaction information indicating an interaction between two proteins in a plurality of proteins, the plurality of databases includes a database having information of the mutant protein generated from a mutant gene, and information of the target protein on which a therapeutic agent directly acts, and searching for the relevance is searching for relevance between a mutant protein and a target protein,
   wherein each piece of the interaction information in the combined database is an action probability indicating relative strength of an interaction, and the action probability is set by machine learning.

9. The relevance searching apparatus according to claim 8, wherein the combined database has graph structure in which the element is a node, and the relevance information is an edge.

10. The relevance searching apparatus according to claim 8, wherein relevance between two elements that are determined to have relevance but do not have direct relevance is presented.

11. The relevance searching apparatus according to claim 8, wherein the plurality of elements is a plurality of pieces of protein information, the relevance information is interaction information indicating an interaction between two proteins in the plurality of proteins, the plurality of databases includes a database having information of the mutant protein generated from a mutant gene, and a database having information of the target protein on which a therapeutic agent directly acts, and searching for the relevance is searching for relevance between a mutant protein and a target protein.

12. The relevance searching apparatus according to claim 8, wherein in the machine learning, learning is performed by using learning data, after an initial value of the action probability is set as beta distribution, and an initial value of an action probability of interaction information that is a target provided with a high action probability is subjected to Bayesian update.

13. The relevance searching apparatus according to claim 12, wherein in the machine learning, for an initial value of an action probability of interaction information analogous to the interaction information that is a target provided with a high action probability, Bayesian update is performed that is weaker than the Bayesian update of the initial value of the action probability of the interaction information that is a target provided with a high action probability.

14. The relevance searching apparatus according to claim 13, wherein the learning data is data of a pair of a mutant protein having a medicinal effect and a target protein.

15. A non-transitory computer-readable storage medium storing a program that causes a computer to execute a process, the process comprising:
- generating a combined database by combining a plurality of databases each including a plurality of elements and relevance information indicating direct relevance between two elements in the plurality of elements; and
- searching for relevance between two elements that do not have direct relevance by using the combined database,
- wherein the plurality of elements is a plurality of pieces of protein information, the relevance information is interaction information indicating an interaction between two proteins in a plurality of proteins, the plurality of databases includes a database having information of the mutant protein generated from a mutant gene, and information of the target protein on which a therapeutic agent directly acts, and searching for the relevance is searching for relevance between a mutant protein and a target protein,
- wherein each piece of the interaction information in the combined database is an action probability indicating relative strength of an interaction, and the action probability is set by machine learning.

* * * * *